United States Patent
Baszczynski et al.

(10) Patent No.: US 6,331,661 B1
(45) Date of Patent: Dec. 18, 2001

(54) METHOD FOR DIRECTIONAL STABLE TRANSFORMATION OF EUKARYOTIC CELLS

(75) Inventors: Christopher L. Baszczynski, Urbandale; Leszek Alexander Lyznik, Johnston; William J. Gordon-Kamm, Urbandale, all of IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 09/193,484

(22) Filed: Nov. 17, 1998

Related U.S. Application Data

(60) Provisional application No. 60/065,613, filed on Nov. 18, 1997, and provisional application No. 60/065,627, filed on Nov. 18, 1997.

(51) Int. Cl.[7] ............... C12N 15/90; C12N 5/04; C12N 15/82; A01H 5/00; A01H 5/10

(52) U.S. Cl. .......... 800/278; 435/69.1; 435/412; 435/419; 435/468; 435/469; 800/288; 800/294; 800/298; 800/317; 800/320; 800/320.1

(58) Field of Search ............ 435/69.1, 320.1, 435/410, 412, 419, 430, 468, 469, 462; 536/23.6; 800/278, 288, 294, 295, 298, 300.1, 320, 320.1, 317

(56) References Cited

U.S. PATENT DOCUMENTS 5,677,177   10/1997   Wahl et al. .

FOREIGN PATENT DOCUMENTS

| | | | |
|---|---|---|---|
| WO92/15694 | 9/1992 | (WO) . | |
| WO93/01283 | 1/1993 | (WO) | C12N/15/00 |
| WO94/17176 | 8/1994 | (WO) . | |
| WO95/00555 | 1/1995 | (WO) . | |
| WO96/04393 | 2/1996 | (WO) . | |
| WO97/09436 | 3/1997 | (WO) | C12N/15/66 |
| WO97/09439 | 3/1997 | (WO) | C12N/15/85 |
| WO97/13401 | 4/1997 | (WO) . | |
| WO97/37012 | 10/1997 | (WO) | C12N/15/11 |
| WO97/47758 | 12/1997 | (WO) . | |
| WO99/23202 | 5/1999 | (WO) | C12N/5/00 |
| WO99/55851 | 11/1999 | (WO) | C12N/15/00 |

OTHER PUBLICATIONS

Brisson et al, Nature, vol. 310, pp. 511–514, 1984.*
Lyzhik et al, Nucl. Acids Res., vol. 24, pp. 3784–3789, 1996.*
Bravo–Angel et al, MPMI vol. 11, pp. 57–63, 1998.*
Tinland et al, EMBO J., vol. 14, pp. 3585–3595, 1995.*
Boulton et al, Plant Mol. Biol., vol. 12, pp. 31–40, 1989.*
Murray et al, Nucl. Acids Res., vol. 17, pp. 477–490, 1989.*
Chui et al, Curr. Biol., vol. 6, pp. 325–330, 1996.*
Ugaki et al, Nucl. Acids Res., vol. 19, pp. 371–377, 1991.*
Seibler et al. (1997) "Double–Reciprocal Crossover Mediated by FLP–Recombinase: A Concept and an Assay", Biochemistry 36:1740–1747.
Snaith et al. (1995) "Multiple Cloning Sites Carrying loxP and FRT Recognition Sites for the Cre and Flp Site–Specific Recombinases", Gene 166:173–174.
Ow et al. (1995) "Genome Manipulation Through Site–Specific Recombination", Critical Reviews in Plant Sciences 14(3):239–261.
Sauer (1992) "Identification of Cryptic lox Sites in the Yeast Genome by Selection for Fre–mediated Chromosome Translocations that Confer Multiple Drug Resistance", J. Mol. Biol. 223I:911–928.
Senecoff et al. (1988) "DNA Recognition by the FLP Recombinase of the Yeast 2 $\mu$ Plasmid", J. Mol. Biol. 201:406–421.
Narasimhulu et al., Early Transcription of Agrobacterium T–DNA Genes in Tobacco and Maize, The Plant Cell, May 1996, pp. 873–886, vol. 8, American Society of Plant Physiologists.
Campbell et al., Codon Usage in Higher Plants, Green Algae, andCyanobacteria, Plant Physiol., 1990, pp. 1–11, vol. 92, Houghton, Michigan.
Lyznik et al., Activity of Yeast FLP Recombinase in Maize and Rice Protoplasts, Nucleic Acids Research, 1993, pp. 969–975, vol. 21. No. 4, Oxford University Press.
Lyznik et al., FLP–Mediated Recombination of FRT Sites in the Maize Genome, Nucleic Acids Research, 1996, pp. 3784–3789, vol. 24, No. 19, Oxford University Press.
Schlake and Bode, Use of Mutated FLP Recognition Target (FRT) Sites for the Exchange of Expression Cassettes at Defined Chromosomal Loci, Biochemistry, 1994, pp. 12746–12751, vol. 33, American Chemical Society, USA.
Albert et al., Site–specific Integration of DNA into Wild–type and Mutant lox Sites Placed in the Plant Genome, The Plant Journal, 1995, pp. 649–659, vol. 7(4),.
Ow and Medberry, Genome Manipulation through Site–Specific Recombination Critical Reviews in Plant Sciences, 1995, pp. 239–261, vol. 14(3), CRC Press, Inc., USA.
Karreman et al, On the Use of Double FLP Recognition Targets (FRTs) in the LTR of Retroviruses for the Construction of High Producer Cell Lines, Nucleic Acids Research, 1996, pp. 1616–1624, vol. 24(9), Oxford University Press.

(List continued on next page.)

Primary Examiner—David T. Fox
Assistant Examiner—Ashwin Mehta
(74) Attorney, Agent, or Firm—Alston & Bird LLP

(57) ABSTRACT

The present invention is drawn to compositions and methods for introducing nucleotide sequences at preferred genomic target sites in a eukaryotic genome. The compositions comprise transfer cassettes which are flanked by nonhomologous recombination sites. The method involves transforming eukaryotic cells containing target sites utilizing non-integrating transformation methods. The method results in efficient integration of nucleotides into predetermined genetic locations and eliminates random DNA integration.

47 Claims, No Drawings

OTHER PUBLICATIONS

Narasimhulu et al., Early Transcription of Agrobacterium T–DNA Genes in Tobacco and Maize, The Plant Cell, May 1996, pp. 873–886, vol. 8, American Society of Plant Physiologists, USA.

Araki et al., Targeted Integration of DNA Using Mutant lox Sites in Embryonic Stem Cells, Nucleic Acids Research, 1997, pp. 868–872, vol. 25(4), Oxford University Press.

Storici et al., Molecular Engineering with the FRT Sequence of the Yeast 2 $\mu$m Plasmid: [cir°] Segregant Enrichment by Counterselection for 2 $\mu$m Site–specific Recombination, Gene, 1997, pp. 245–255, vol. 195, Elsevier Science B.V.

Albert et al. Site–specific Integration of DNA into Wild–type and Mutant lox Sites Placed in the Plant Genome. The Plant Journal, (1995), pp. 649–659, vol. 7(4). Lawrence Berkeley Laboratories, California.

Araki et al. Targeted Integration of DNA Using Mutant lox Sites in Embryonic Stem Cells. Nucleic Acids Research, (1997), pp. 868–872, vol. 25(4). Oxford University Press.

Bethke et al. Segmental Genomic Replacement by Cre–Mediated Recombination: Genotoxic Stress Activation of the p53 Promoter in Single–Copy Transformants. Nucleic Acids Research, (1997), pp. 2828–2834, vol. 25(14).

Czako et al. (Mar. 1997) Negative Selection Markers for Plants. Technology Transfer of Plant Biotechnology Chapter 6, pp. 67–93; CRC Press, Inc., Columbia, South Carolina.

Dale et al. Gene Transfer with Subsequent Removal of the Selection Gene from the Host Genome. Proc. Natl. Acad. Sci. USA, (Dec. 1991), pp. 10558–10562, vol. 88.

Dasgupta et al. Rice Tungro Bacilliform Virus DNA Independently Infects Rice After Agrobacterium–mediated Transfer. Journal of General Virology, (1991), pp. 1215–1221, vol. 72. Great Britain.

Feil et al. Regulation of Cre Recombinase Activity by Mutated Estrogen Receptor Ligand–Binding Domains. Biochemical and Biophysical Research Communications, (1997), pp. 752–757, vol., 237. Academic Press.

Golic et al. FLP–Mediated DNA Mobilization to Specific Target Sites in Drosophila Chromosomes. Nucleic Acids Research, (1997), pp. 3665–3671, vol. 25(18). Oxford University Press.

Grimsley et al. Meristematic Tissues of Maize Plants Are Most Susceptible to Agroinfection with Maize Streak Virus. Bio/Technology, (Feb. 1988), pp. 185–189, vol. 6. Friedrich Miescher–Institut, Switzerland.

Kilby et al. FLP Recombinase in Transgenic Plants: Constitutive Activity in Stably Transformed Tobacco and Generation of Marked Cell Clones in Arabidopsis. The Plant Journal, (1995), pp. 637–652, vol. 8(5).

Logie et al. Ligand–regulated site–specific Recombination. Proc. Natl. Acad. Sci USA, (Jun. 1995), pp. 5940–5944, vol. 92.

Louie Vascular Puncture of Maize Kernels for the Mechanical Transmission of Maize White Line Mosaic Virus and Other Viruses of Maize. (1995), pp. 139–143, vol. 85(2). The American Phytopathological Society.

Lyznik et al. Activity of Yeast FLP Recombinase in Maize and Rice Protoplasts. Nucleic Acids Research, (1993), pp. 969–975, vol. 21(4). Oxford Univerity Press.

Lyznik et al. FLP–mediated Recombination of FRT sites in the Maize Genome. Nucleic Acids Research, (1996), pp. 3784–3789, vol. 24(19). Oxford University Press., India.

Lyznik et al. Heat–inducible Expression of FLP Gene in Maize Cells. The Plant Journal, (1995), pp. 177–186, vol. 8(2).

McLeod et al. Identification of the Crossover Site during FLP–Mediated Recombinationi in the Saccharomyces cerevisiae Plasmid 2 $\mu$m Circle. Molecular and Cellular Biology, (Oct. 1986), pp. 3357–3367, vol. 6(10). The American Society for Microbiology, Cold Spring Harbor, New York.

Narasimhulu at al. Early Transcription of Agrobacterium T–DNA Genes in Tobacco and Maize. The Plant Cell, (May 1996), pp. 873–886, vol. 8. American Society of Plan Physiologists.

O'Gorman et al. Protamine–Cre Recombinase Transgenes Efficiently Recombine Target Sequences in the Male Germ Line of mice, but not in Embryonic Stem Cells. Proc. Natl. Acad. Sci. USA, (Dec. 1997), pp. 14602–14607, vol. 94.

O'Gorman et al. Recombinase–Mediated Gene Activation and Site–Specific Integration in Mammalian Cells. Science, (Mar. 15, 1991), pp. 1351–1355, vol. 251. The Salk Institute for Biological Studies, La Jolla, California.

Russell et al. Directed Excision of a Transgene from the Plant Genome. Mol. Genet., (1992), pp. 49–59, vol. 234. MGG.

Schlake et al. Use of Mutated FLP Recognition Target (FRT) Sites for the Exchange of Expression Cassettes at Defined Chromosomal Loci. Biochemistry, (1994), pp. 12746–12751, vol. 33. American Chemical Society.

Scholthof et al. Plant Virus Gene Vectors for Transient Expression of Foreign Proteins in Plants. Annu. Rev. of Phytopathol., (1996), pp. 299–323, vol. 34. Annual Reviews Inc.

Senecoff et al. Directionality in FLP Protein–promoted Site–specific Recombination Is Mediated by DNA–DNA Pairing. The Journal of Biological Chemistry, (Jun. 5, 1986), pp. 7380–7386, vol. 261(16), The American Society of Biological Chemists, Inc..

Timmermans et al. Trans Replication and High Copy Numbers of Wheat Dwarf Virus Vectors in Maize Cells. Nucleic Acids Research, (1992), pp. 4047–4054, vol. 20(15). Oxford University Press.

Ugaki et al. Replication of a Geminivirus Derived Shuttle Vector in Maize Endosperm Cells. Nucleic Acid Research, (1991), pp. 371–377, vol. 19(2). Oxford University Press.

Umlauf et al. The Functional Significance of DNA Sequence Structure in a Site–specific Genetic Recombination Reaction. (Mar. 1988), pp. 1845–1852. IRL Press Limited, Oxford, England.

Zhang et al. Inducible site–directed Recombination in Mouse Embryonic Stem Cells. Nucleic Acids Research, (1996), pp. 543–548, vol. 24. Oxford University Press.

* cited by examiner

METHOD FOR DIRECTIONAL STABLE TRANSFORMATION OF EUKARYOTIC CELLS

CROSS-REFERENCE TO RELATED APPLICATION

This application claims the benefit of U.S. application Ser. No. 60/065,613, filed Nov. 18, 1997, and U.S. application Ser. No. 60/065,627, filed Nov. 18, 1997, both of which are herein incorporated by reference.

FIELD OF THE INVENTION

The invention relates to the genetic modification of eukaryotes. Particularly, the control of gene integration and expression in plants is provided.

BACKGROUND OF THE INVENTION

Genetic modification techniques enable one to insert exogenous nucleotide sequences into an organism's genome. A number of methods have been described for the genetic modification of plants. All of these methods are based on introducing a foreign DNA into the plant cell, isolation of those cells containing the foreign DNA integrated into the genome, followed by subsequent regeneration of a whole plant. Unfortunately, such methods produce transformed cells that contain the introduced foreign DNA inserted randomly throughout the genome and often in multiple copies.

The random insertion of introduced DNA into the genome of host cells can be lethal if the foreign DNA happens to insert into, and thus mutate, a critically important native gene. In addition, even if a random insertion event does not impair the functioning of a host cell gene, the expression of an inserted foreign gene may be influenced by "position effects" caused by the surrounding genomic DNA. In some cases, the gene is inserted into sites where the position effects are strong enough to prevent the synthesis of an effective amount of product from the introduced gene. In other instances, overproduction of the gene product has deleterious effects on the cell.

Transgene expression is typically governed by the sequences, including promoters and enhancers, which are physically linked to the transgene. Currently, it is difficult to precisely modify the structure of transgenes once they have been introduced into plant cells. In many applications of transgene technology, it would be desirable to introduce the transgene in one form, and then be able to modify the transgene in a defined manner. By this means, transgenes could be activated or inactivated where the sequences that control transgene expression can be altered by either removing sequences present in the original transgene or by inserting additional sequences into the transgene.

Therefore, it is essential to gain more control over foreign DNA integration into the nuclear genome of plant cells to expedite the efficient production of transgenic plants with stable and reliable expression of transgenic traits. Relatively low frequency and randomness of foreign DNA integration make genetic transformation a labor-intensive and unpredictable procedure. Multi-copy, random integrations of transforming DNA molecules frequently lead to aberrant expression of foreign genes, affect expression of endogenous genes, and provide transgenic organisms with unstable transgenic traits. All plant transformation procedures currently in use take advantage of biochemical pathway(s) involving random, illegitimate recombination to integrate foreign DNA. Illegitimate recombinations constitute the intrinsic property of a conventional genetic transformation process. As such, desired DNA integration events cannot be separated, or preferably selected for, from among any excessive random integrations, unless a different mechanism governs the integration of productive events.

One approach for gene targeting, which is extensively pursued, involves the use of DNA homologous recombination for integration of foreign DNA into pre-selected genomic locations. The process involves both productive (homologous, targeted) and non-productive (illegitimate, random) integrations. Innovative strategies have already been proposed to reduce, or eliminate random integration of targeting vectors. They include the use of negative selection markers to eliminate random integrations by selection against actively expressed foreign genes, excisions of randomly integrated copies of foreign genes by the use of site-specific recombinations, or identification and application of specific inhibitors of non-homologous recombinations such as poly-(ADP-ribosylation) inhibitors.

The basic problem with current gene targeting procedures, however, is that the efficiency of homologous recombination in somatic cells of higher eukaryotes is extremely low being about 1,000-, 1,000,000-fold less frequent than illegitimate, random integrations. Taking into account that random integrations are barely considered satisfactory in the conventional genetic transformation procedures, routine gene targeting is presently not practical, at least in plant genetic transformation systems. Therefore, methods to control targeting and integration of foreign genes into the genome are needed.

SUMMARY OF THE INVENTION

Compositions and methods for introducing nucleotide sequences only at preferred genomic target sites are provided. The compositions comprise transfer cassettes which incorporate site-specific recombination sequences. The method involves transforming eukaryotic cells containing target sites utilizing transformation vectors which do not integrate genomic DNA, or integrate at very low frequency, unless provided with a site-specific integration system. The method results in efficient integration of nucleotides into predetermined genetic locations and minimizes or precludes random DNA integration.

DETAILED DESCRIPTION OF THE INVENTION

Compositions and methods for introducing nucleotide sequences into predetermined genomic target sites in a plant genome is provided. The methods preclude the random integration of DNA into the genome. The methods use novel recombination sites in a gene targeting system which facilitates directional targeting of desired genes and nucleotide sequences into corresponding recombination sites previously introduced into the target genome. Methods for the production of transgenic plants containing specific recombination sites integrated in the plant genome are described in co-pending patent application entitled "Compositions and Methods for Genetic Modification of Plants" application Ser. No. 09/193,502 filed Nov. 17, 1998, now U.S. Pat. No. 6,187,994. filed concurrently herewith and herein incorporated by reference.

Generally, for targeted insertion of nucleotide sequences, two non-identical recombination sites are introduced into the target organism's genome establishing a target site for insertion of nucleotide sequences of interest. These recombination sites may flank other nucleotide sequences. Once a stable plant or cultured tissue is established a second construct, or nucleotide sequence of interest, flanked by corresponding recombination sites as those flanking the target site, is introduced into the stably transformed plant or tissues in the presence of a recombinase protein. This process results in exchange of the nucleotide sequences between any two identical recombination sites of the target site and the transfer cassette.

It is recognized that the transformed organism may comprise multiple target sites; i.e., sets of non-identical recombination sites. In this manner, multiple manipulations of the target site in the transformed organism are available. By target site in the transformed organism is intended the DNA sequence that has been inserted into the transformed organism's genome and comprises the non-identical recombination sites.

Examples of recombination sites for use in the invention are known in the art and include FRT sites (See, for example, Schlake and Bode (1994) *Biochemistry* 33:12746–12751; Huang et al. (1991) *Nucleic Acids Research* 19:443–448; Paul D. Sadowski (1995) In Progress in Nucleic Acid Research and Molecular Biology vol. 51, pp. 53–91; Michael M. Cox (1989) *In Mobile DNA,* Berg and Howe (eds) American Society of Microbiology, Washington D.C., pp. 116–670; Dixon et al. (1995) 18:449458; Umlauf and Cox (1988) *The EMBO Journal* 7:1845–1852; Buchholz et al. (1996) *Nucleic Acids Research* 24:3118–3119; Kilby et al. (1993) Trends Genet. 9:413–421: Rossant and Geagy (1995) *Nat. Med.* 1: 592–594; *Lox Albert et al. (1995) The Plant J.* 7:649–659: Bayley et al. (1992) *Plant Mol. Biol.* 18:353–361; Odell et al. (1990) *Mol. Gen. Genet.* 223:369–378; and Dale and Ow (1991) *Proc. Natl. Acad. Sci. USA* 88:10558–105620; Qui et al. (1994) *Proc. Natl. Acad. Sci. USA* 91:1706–1710; Stuurman et al. (1996) *Plant Mol. Biol.* 32:901–913; and Dale et al. (1990) *Gene* 91:79–85; all of which are herein incorporated by reference.)

By "target site" is intended a predetermined genomic location within the nucleus where the integration of a specific transformed nucleotide sequence is to occur. The target site of the invention is characterized by being flanked by non-identical recombination sites corresponding to the non-identical recombination sites flanking the nucleotide sequence to be transformed into the cell, (the transfer cassette), and integrated into the genome. The non-identical recombination sites in combination with recombinase activity result in a recombination event between the non-identical recombination sites of the target site and the target cassette (the integrating sequence). This event produces an integrated nucleotide sequence into the specified genomic location.

To practice the methods of the invention, a transformed organism, particularly a plant, of interest containing a target site integrated into its genome is needed. The target site is characterized by being flanked by non-identical recombination sites. A targeting cassette is additionally required containing a nucleotide sequence flanked by corresponding non-identical recombination sites as those sites contained in the target site of the transformed organism. A recombinase which recognizes the non-identical recombination sites and catalyzes site-specific recombination is required.

By non-identical recombination sites is intended that the flanking recombination sites are not identical. That is, one flanking recombination site may be a FRT site (SEQ ID NOS: 1 and 2) where the second recombination site may be a mutated FRT site (SEQ ID NOs: 2, 3, 4 and 5). The non-identical recombination sites used in the methods of the invention prevent or greatly suppress recombination between the two flanking recombination sites and excision of the nucleotide sequence contained therein. Accordingly, it is recognized that any suitable non-identical recombination sites may be utilized in the invention, including FRT and mutant FRT sites, FRT and lox sites, lox and mutant lox sites, as well as other recombination sites known in the art.

By suitable non-identical recombination site implies that in the presence of active recombinase, excision of sequences between two non-identical recombination sites occurs, if at all, with an efficiency considerably lower than the recombinationally-mediated exchange targeting arrangement of nucleotide sequences into the plant genome. Thus, suitable non-identical sites for use in the invention include those sites where the efficiency of recombination between the sites is low; for example, where the efficiency is less than about 30 to about 50%, preferably less than about 10 to about 30%, more preferably less than about 5 to about 10%, even more preferably less than about 1 %.

As noted above, the recombination sites in the targeting cassette correspond to those in the target site of the transformed organism. That is, if the target site of the transformed organism contains flanking non-identical recombination sites of FRT and a mutant FRT, the targeting cassette will contain the same FRT and mutant FRT non-identical recombination sites.

It is furthermore recognized that the recombinase, which is used in the invention, will depend upon the recombination sites in the target site of the transformed organism and the targeting cassette. That is, if FRT sites are utilized, the FLP recombinase will be needed. In the same manner, where lox sites are utilized, the Cre recombinase is required. If the non-identical recombination sites comprise both a FRT and a lox site, both the FLP and Cre recombinase will be required in the plant cell.

The present invention utilizes nonintegrating vectors and methods of introducing transfer cassettes into the genome of the organism of interest. In this manner, efficient site specific integration of exogenous nucleotide sequences is promoted and random insertion is avoided. By efficient site specific DNA integration is intended the maximization of recombination events between the introduced integrating sequence and the predetermined genomic target sites of transformed cells. That is, the methods prevent random DNA integration and insertion of DNA into sites other than the intended target site within the eukaryotic genome. Prevention of random integration is accomplished through the utilization of non-integrating nucleic acid molecules in association with the gene targeting method set forth in the copending application disclosed above.

The methods of the invention can be used to target nucleotide sequences into any eukaryote. By eukaryote is intended to mean any higher eukaryotic organism, more specifically plants and even more specifically monocotyledonous plants.

Transient transformation methods for plants are available in the art and include DNA delivery systems which are capable of introducing nucleotide sequences into a eukaryotic cell, where these sequences either contain no homology to the genomic sequence of the target cell or have been modified in a way that precludes their own recombination or integration into the genome. Such non-integrative DNA delivery systems include the use of Agrobacterium for monocots, modified Agrobacterium-mediated T-DNA transfer for dicots, and viral vectors. These systems can effectively deliver DNA into plant cells without random integration. Thus, the nucleotide sequences are only or preferably able to insert at predetermined target sites and under suitable conditions such as those provided in copending application "Compositions and Methods for Genetic Modification of Plants". Thus, by non-integrating methods are intended methods of introducing nucleotide sequences into a cell without subsequent random integration or with minimum random integration. Random integration refers to integration or insertion of the nucleotide sequences at sites other than at corresponding target sites.

The development of plant virus gene vectors for expression of foreign genes in plants provides a means to provide high levels of gene expression within a short time. The benefits of virus-based transient RNA and DNA replicons include rapid and convenient engineering coupled with flexibility for expeditious application in various plant species. In this manner, autonomously replicating viruses offer numerous advantages for use as vehicles for transient expression of foreign genes, including their characteristic high levels of multiplication and concomitant levels of transient gene expression. Such viruses include but are not limited to Bromovirus, Caulimovirus, Furovirus, Geminivirus, Hordeivirus, Potexvirus, Tobamovirus, Tobravirus, Tombusvirus, Potyvirus, Comovirus, Alfamovirus, Dianthovirus, etc. See, for example, Ugaki et al. (1991) *Nucleic Acids Res.* 19:371–377; Timmermans et aL (1992) *Nucleic Acids Res.* 20:40474054; Louie, Raymond (1995) Phytopathology 85:139–143; Scholthof et al. (1996) *Annu. Rev. Phytopathol.*34:299–323, and the references cited therein, all of which are herein incorporated by reference.

Viral methods use viral vectors that replicate as extrachromosomal DNA, or RNA molecules. Shuttle vectors may be constructed that contain viral sequences critical to replication. Such vectors can be used to introduce transfer cassettes containing nucleotide sequences into plants and plant cells. Such vectors, which have included viral genomic DNA from the geminiviruses (wheat dwarf virus or maize streak virus) can be transformed into monocotyledonous plants and propagate in the plant cell nucleus to high copy numbers (Timmermans et al. (1992) *Nucleic Acids Res.* 20:4047–4054). Once viral particles are in the plant cell, they can accumulate to high copy numbers which will increase the probability that a recombination event will occur between the non-identical recombination sites flanking the target sequence, leading to a successful integration of the nucleotide sequence of interest.

Agrobacterium-mediated gene transfer exploits the natural ability of *Agrobacterium tumefaciens* to transfer DNA into plant cells. Agrobacterium is a plant pathogen that transfers a set of genes encoded in a region called T-DNA of the Ti plasmid into plant cells at wound sites. The typical result of gene transfer is a tumorous growth called a crown gall in which the T-DNA is stably integrated into a host chromosome. The ability to cause crown gall disease can be removed by deletion of the genes conferring tumorigenesis in the T-DNA without loss of DNA transfer and integration. The DNA to be transferred is attached to border sequences that define the end points of an integrated T-DNA.

Agrobacterium-based transformation methods may also be used in the invention. The Agrobacterium system can be used to introduce transfer cassettes into monocotyledonous plant cells to take advantage of the inability of T-DNA to efficiently integrate into the genome of monocot plants. It is known that in nature Agrobacterium does not transform monocots. Thus, supervirulent strains of Agrobacterium have been developed to utilize Agrobacterium as a vector to transform monocots. The present invention takes advantage of the ability of the Agrobacterium system to introduce transfer cassettes into monocot cells without the ability to direct incorporation of the transferred sequence into the monocot genome. It has been demonstrated that the Agrobacterium system can be used to transfer DNA from the bacteria to the plant cell. See, for example Grimsley et al. (1988) *BioTechnology* 6:185–189; Dasgupta et al. (1991) *J. Gen. Virol.* 72:1215–1221; and the references cited therein.

It is further recognized that Agrobacterium based transfer systems may be modified such that the Agrobacterium directs introduction and transient expression of the transferred DNA (in this instance the transfer cassette), but is unable to direct efficient integration of T-DNA into the genome of the plant. Such modified Agrobacterium systems are available in the art. See, for example, Narasimhulu et al. (1996) *The Plant Cell* 8:873–886, herein incorporated by reference. Narasimhulu et al. demonstrate that the C-terminal nuclear localization signal of the VirD2 protein is not essential for nuclear uptake of T-DNA and further show that the t domain of VirD2 is required for efficient integration of T-DNA into the plant genome. Thus, mutations into this region will allow introduction and transient expression of the transfer cassette but avoid unwanted random insertion. For example, a nonpolar transposon insertion into the C-terminal coding region of virD2 resulted in only slightly decreased production of MRNA, although this insertion resulted in the loss of the nuclear localization sequence the ω region from VirD2 protein and rendered the bacterium avirulent. Thus, the modified Agrobacterium is particularly beneficial for use in dicots.

The non-integrating transformation methods can be used to introduce the transfer cassettes into any plant cell. In this manner, genetically modified plants, plant cells, plant tissue, seed, and the like can be obtained. Transformation protocols may vary depending on the type of plant or plant cell, i.e. monocot or dicot, targeted for transformation.

Once the transfer cassettes have been introduced into the plant, the flanking non-identical recombination sites of transfer cassettes recombine with corresponding sites of the target within the plant genome. The cells having a modified genome may be grown into plants in accordance with conventional approaches. See, for example, McCormick et al. (1986) *Plant Cell Reports,* 5:81–84. These regenerated plants may then be pollinated with either the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

Because of the use of non-integrating means of introducing transfer cassettes provided herein, the plants of the invention may be distinguishable from other transformation methods as the modified plants of the invention will contain nucleotide sequences of interest inserted into the plant genome only or substantially at target sites. By substantially at target sites, is intended that target cassettes are inserted into the genome only about five times at non-target sites, preferably less than about three times, more preferable about one time or less.

It is recognized that the methods of the invention can additionally be used in other eukaryotic cells for efficient insertion of nucleotide sequences of interest, including mammalian cells. In this manner, target sites can be introduced into a cell line and non-integrating methods used to introduce transfer cassettes into the cells. This provides an efficient means of introducing genes of interest into animals, particularly agricultural animals.

Viral means of introducing DNA into mammalian cells are known in the art. In particular, a number of vector systems are known for the introduction of foreign or native genes into mammalian cells. These include SV40 virus (See, e.g., Okayama et al. (1985) *Molec. Cell Biol.* 5:1136–1142); Bovine papilloma virus (See, e.g., DiMaio et al. (1982) *Proc. Natl. Acad. Sci. USA* 79:4030–4034); adenovirus (See, e.g., Morin et al. (1987) *Proc. Natl. Acad. Sci. USA* 84:4626; Yifan et al. (1995) *Proc. Natl. Acad. Sci. USA* 92:1401–1405; Yang et al. (1996) *Gene Ther.* 3:137–144; Tripathy et al. (1996) *Nat. Med.* 2:545–550; Quantin et al. (1992) *Proc. Natl. Acad. Sci. USA* 89:2581–2584; Rosenfeld et al. (1991) *Science* 252:431–434; Wagner (1992) *Proc. Natl. Acad. Sci. USA* 89:6099–6103; Curiel et aL (1992) *Human Gene Therapy* 3:147–154; Curiel (1991) *Proc. Natl. Acad. Sci. USA* 88:8850–8854; LeGal LaSalle et al. (1993) *Science* 259:590–599); Kass-Eisler et al. (1993) *Proc. Natl. Acad. Sci. USA* 90:11498–11502); adeno-associated virus (See, e.g., Muzyczka et al. (1994) *J. Clin. Invest.* 94:1351; Xiao et al. (1996) *J. Virol.* 70:8098–8108); herpes simplex virus (See, e.g., Geller et al. (1988) *Science* 241:1667; Huard et al. (1995) *Gene Therapy* 2:385–392; U.S. Pat. No. 5,501, 979); retrovirus-based vectors (See, for example, Curran et al. (1982) *J. Virol.* 44:674–682; Gazit et al. (1986) *J. Virol.* 60:19–28; Miller, A. D. (1992) *Curr. Top. Microbiol. Immunol.* 158:1–24; Cavanaugh et al. (1994) *Proc. Natl. Acad. Sci. USA* 91:7071–7075; Smith et al. (1990) *Molecular and Cellular Biology* 10:3268–3271); herein incorporated by reference. See also, Wu et al. (1991) *J. Biol. Chem.* 266:14338–14342; Wu and Wu (*J. Biol Chem.* (1988)) 263:14621–14624; Wu et al. (1989) *J. Biol. Chem.* 264:16985–16987; Zenke et al. (1990) *Proc. Natl. Acad. Sci. USA* 87:3655–3659; Wagner et al. (1990) 87:3410–3414.

Standard techniques for the construction of the vectors of the present invention are well-known to those of ordinary skill in the art and can be found in such references as Sambrook et al., *Molecular Cloning: A Laboratory Manual*, 2nd ed. (Cold Spring Harbor, N.Y., 1989). A variety of strategies are available for ligating fragments of DNA, the choice of which depends on the nature of the termini of the DNA fragments and which choices can be readily made by those of skill in the art.

The following examples are offered by way of illustration not by way of limitation.

EXPERIMENTAL

Example 1

Creation of Novel Non-identical FRT Sites

DNA fragments containing novel FRT sequences are constructed either by synthesizing, annealing and ligating complementary oligonucleotides or by creating primers for PCR amplification of a DNA product containing the new FRT sequence near the 5' end of the PCR product. The newly constructed FRT product includes flanking restriction sites useful for cloning into plant expression units. In general, the 5' end is flanked by an NheI site and a terminal NcoI site. The NcoI site includes the bases ATG, which are advantageously used in newly developed vector constructs as the recognition sequence to initiate an open reading frame. In sequence-based constructs designated noATG/FRT, the NheI site is used for cloning thereby eliminating the upstream ATG in the process. At the 3' end of the FRT sequence, a restriction site is included enabling unique identification of the individual spacer sequences. As specific examples, the wild type FRT site (designated FRT1 here, SEQ ID NO: 2) is cloned with a flanking BglII site, the FRT5 site (spacer TTCAAAAG) has a ScaI site, the FRT6 site (SEQ ID NO: 4, spacer TTCAAAAA) has an AatII site, and the FRT7 site (SEQ ID NO: 5) spacer TTCAATAA) has an SpeI site. The outermost flanking restriction site is an XhoI site and is used to clone a gene of interest into the open reading frame.

The structures and sequences of the FRT sites as designed and/or used in the present invention example are depicted below with positions of restriction sites, repeats and spacer regions indicated.

```
FRT1 (SEQ ID NO: 2)
   NcoI NheI     Repeat 1       Repeat 2      Spacer   Inverted Repeat BglIIXhoI
5'CCATGGCTAGC GAAGTTCCTATTCC GAAGTTCCTATTC TCTAGAAA GTATAGGAACTTC AGATCTCGAG FRT5 (SEQ ID NO: 3)
   NcoI NheI     Repeat 1       Repeat 2      Spacer   Inverted Repeat ScaI XhoI
5'CCATGGCTAGC GAAGTTCCTATTCC GAAGTTCCTATTC TTCAAAAG GTATAGGAACTTC AGTACTCGAG FRT6 (SEQ ID NO: 4)
   NcoI NheI     Repeat 1       Repeat 2      Spacer   Inverted Repeat  AatII XhoI
5'CCATGGCTAGC GAAGTTCCTATTCC GAAGTTCCTATTC TTCAAAAA GTATAGGAACTTC AGACGTCCTCGAG FRT7 (SEQ ID NO: 5)
   NcoI NheI     Repeat 1       Repeat 2     Spacer    Inverted Repeat SpeI XhoI
5'CCATGGCTAGC GAAGTTCCTATTCC GAAGTTCCTATTCTTCAATAA GTATAGGAACTTCACTAGTTCTCGAG
```

Example 2

Creation of Agrobacterium Plant Transformation Vectors Containing Novel Non-identical FRT Sites for Dicots.

Bacterial Strains and Growth Conditions

*Escherichia coli* strains are grown at 37° C. on Luria-Bertani medium (Maniatis, et al.(1982) Molecular Cloning: A Laboratory Manual (Cold Spring Harbor, N.Y.: Cold Spring Harbor Laboratory)) and *Agrobacterium tumefaciens* strains at 30° C. on AB-sucrose minimal medium (Lichtenstein, et al. (1986) Genetic engineering of plants, in *DNA Cloning: A Practical Approach*, Vol. 2, D. M. Glover, ed. (Oxford, UK: IRL Press), pp. 67–119) containing the appropriate antibiotics. Antibiotic concentrations (µg/mL) are as follows: ampicillin, 100; kanamycin, 20 for *E. coli*; carbenicillin, 100; kanamycin, 100; spectinomycin, 100; rifampicin, 10 for Agrobacterium.

Construction of pBISN1 and Its Derivatives

To construct the transferred (T)-DNA binary vectors, one can clone an EcoRI-SalI fragment of pCNL65 (Liu et al.

(1992) *Plant Mol. Biol.* 20:1071–1087), containing a β-glucuronidase gusA gene with the ST-LS1 second intron (Vancanneyt et al. (1990) *Mol. Gen. Genet.* 220:245–250), into pBluescript SK+ (Stratagene). This plasmid is digested with Xho1 (upstream of the gusA gene), the overhanging ends filled in, using the Klenow fragment of DNA polymerase I and nucleotide triphosphates, and the gusA-intron gene using Sac1 is released. The gusA gene (lacking an intron) from pE1120 (Ni et al. (1995) *Plant J.* 7:661–676) is removed by using Sma1 and Sac1 and replaced with the gusA-intron gene fragment described above. The final plasmid will contain T-DNA border repeat sequences, a nopaline synthase-neomycin phosphotransferase II gene for selection of kanamycin-resistant transgenic plants, and a gusA-intron gene under the regulation of the promoter from pE1120.

Based on the design of FRT sites as described above, various methods such as PCR, mutagenesis and/or other standard cloning protocols can be used to introduce the FRT sites into desired locations in the plasmid above during the vector creation process. Example methods are described in a co-pending patent application entitled "Compositions and Methods for Genetic Modification of Plants" filed concurrently herewith and herein incorporated by reference.

The plasmid described above is placed into an IncW replicon as described by Narisasimhulu et al. (1996) *The Plant Cell* 8:873–886, herein incorporated by reference.

The plasmid is mobilized into Agrobacterium strains, using a triparental mating procedure (Figurski and Helinski (1979) *Proc. Natl. Acad. Sci. USA* 76:1648–1652) and the mobilizing plasmid pRK2013 (Ditta et al. (1980) *Proc. Natl. Acad. Sci. USA* 77:7347–7351). The trans-conjugants are selected on AB-sucrose minimal medium containing rifampicin and kanamycin or rifampicin and spectinomycin. Alternatively, the Agrobacterium binary system as described by Bevan, M. (1984) *Nucl. Acids Res.* 12:8711–8721; herein incorporated by reference.

Growth and Infection of Plant Cells and Determination of GUS Activity

Nicotiana tabacum BY-2 cells are propagated in Murashige and Skoog medium (Gibco BRL) containing 3% sucrose, 1 µg/mL thiamine, 0.2 µg/mL 2,4-D, and 370 µg/mL $KH_2PO_4$. Zea mays Black Mexican Sweet (BMS) cells are propagated in Murashige and Skoog medium containing 2% sucrose, 2 µg/mL 2,4-D, 0.2 mg/mL myoinositol, 0.13 mg/mL L-asparagine, 0.13 µg/mL nicotinic acid, and 0.25 µg/mL each of thiamine, pyridoxine, and pantothenic acid. The cultures are shaken at 140 rpm at 25° C. in continuous light.

To infect plant cells, virulence (vir) gene activity is induced in Agrobacterium with acetosyringone. Agrobacterium cells are grown to a density of $2 \times 10^9$ cells per mL (A=100, using a Klett-Summerson spectrophotometer, red filter) in AB-sucrose medium. The cells are centrifuged at 10,000 g, suspended at a concentration of $1 \times 10^9$ cells per mL (A=50) in induction medium (AB salts, 0.5 % glucose, 2mM sodium phosphate, 50 mM Mes, pH 5.6, 50 µM acetosyringone), and incubated with gentle shaking at 25° C. for 14 to 18 hr. After washing the bacterial cells in plant culture medium, plant cells are inoculated with induced Agrobacterium (~20 bacterial cells per plant cell, except where noted otherwise) and cocultivated at 25° C. with shaking at 140 rpm for various periods of time. Most of the bacteria is washed off by centrifugation of the cocultivation mixture at 300 rpm (model GLC-2 clinical centrifuge; Beckman Sorvall, Newtown, Conn.) for 2 min. The plant cell pellet is suspended and washed once more in plant culture medium and then resuspended in culture containing either 100 µg/mL timentin or 200 µg/mL cefotaxime. To collect plant cells for isolation of RNA, the cells are washed three times, as described above, in plant culture medium. RNA is extracted from these cells either directly after harvesting (either of the two methods listed below) or after freezing in liquid nitrogen and storage at −70° C. (TRIzol reagent [Gibco BRL] extraction method).

The percentage of cells expressing GUS activity is determined by incubating the cells in GUS histochemical staining solution (50 mM $NaH_2PO_4$, 10 mM $Na_2$; EDTA, 0.3 M mannitol, 20% methanol, and 1 mM 5-bromo4-chloro-3-indolyl β-D-glucuronic acid [X-gluc] overnight at 37° C. (Kosuge et al.(1990) *Plant Sci.* 70:133–140).

Example 3

Creation of Agrobacterium Plant Transformation Vectors Containing Novel Non-identical FRT Sites for Monocots Agrobacterium-mediated DNA transfer to maize is roughly as efficient as it is to dicotyledenous plants in different, but functionally equivalent agroinfection systems. See, Grinsley et al. (1987) Agroinfection, p. 87–107. In: *Plant DNA Infectious Agents.* Hohn and Schell (Eds.) Springer, New York and Vienna. This observation questions the definition of the host/parasite interaction, since the steps up to and including DNA transfer do seem to occur in a plant that does not produce tumors.

Experimental Protocol

Plasmid constructions, bacterial strains and media. Construction of the transferred (T)-DNA binary vectors including incorporation of FRT sites is essentially as described in Example 2. Plasmids are maintained in *Escherichia coli* strain DH1 (Maniatis and Sambrook (1982) Molecular Cloning: A Laboratory Manual. (Cold Spring Harbor, N.Y.: Cold Spring Harbor Laboratory)) at 37° C. or in *A. tumefaciens* strain C58 (Holsters et al. (1980) *Plasmid* 3:212–230) at 28° C. The strain C58(pTiC58,pEAP37) carrying a dimer of MSV genomes in the T-DNA of a binary vector has been described (Grimsley et al. (1987) *Nature* 325:177–179). C58(pGV3850::pEAP25) is constructed by (i) cutting pMSV12 (Grimsley et al. (1987) supra) at its unique Sa1I site, (ii) cutting pEAP1, a 7.6kb large mobilizable plasmid encoding bacterial resistances for ampicillin and kanamycin and a kanamycin resistance gene expressed in plants with Sa1I, (iii) ligating (i)+(ii) to produce a plasmid, PHMI, which could be selected in *E. coli* by ampicillin, kanamycin and chloramphenicol resistance, and (iv) mobilization (Rogers et al. (1986) *Meth. Enzymol.* 118:627–640) of the plasmid PHMI to C58(pGV3850) (Zambryski et al.(1983) *EMBO J.* 2:2143–2150) producing C58(pGV3850::PHMI). Restriction enzyme digestions and ligations are done under conditions recommended by the manufacturer (Biofinex, Switzerland). Prior to inoculation, strains of Agrobacterium are streaked out on YEB (Grimsley et al. (1986) *Proc. Natl. Acad. Sci. USA*, 83:3282–3286) plates solidified with 1.5% agar and supplemented with 100 µg/ml rifampicin and 25 µg/ml kanamycin and allowed to grow for 48 h. A single colony is used to inoculate 10 ml of liquid YEB medium in a 100 ml Erlenmeyer flask supplemented with antibiotics as previously. Growth is continued with shaking at 200 r.p.m. for 24 h, then 500 µl of this culture is used to inoculate a similar flask and growth continued for a further 20 h. This procedure yields a final density of viable Agrobacterium cells in the region of $10^9$/ml (estimated by plating). The cells are then harvested by centrifugation and resuspended in an equal volume of 10 mM $MgSO_4$ without antibiotics; such a suspension is subsequently referred to as undiluted or $10°$ dilution; for experiments involving a dilution series 10 mM $MgSO_4$ was also used as the diluent.

Growth of plants: Maize seeds for 10-day old plants are sown in pots in a phytotron in a 12 hour light/dark cycle at 25° C. in a light intensity of about 10000 lux (Sylvania 215 W fluorescent lamps type F96T12/CW/VHO) then moved to the BL3 containment laboratory immediately prior to inoculation; subsequent growth conditions have been described (Grimsley et al. (1987) Nature 325:177–179). Three-day old seedlings are prepared by (i) sterilization by stirring for 20 min in 0.7% calcium hypochlorite solution, (ii) washing three times (stirring for 20 min each time) in sterile distilled water (iii) preparing 9 cm diameter presterilized Petri dishes with 3 sheets of sterile 8.5 cm diameter Macherey-Nagel (Germany) filter paper in the bottom and ca. 10 ml of sterile water per dish, (iv) putting ca. 20 seeds into each geranium dish, and (v) incubating in the dark at 28° C. for 3 days, or until the distance between the scutellar node and the apical tip of the coleoptiles is 1–2 cm.

Inoculation of plants: For injections, a 50 $\mu$l or a 100 $\mu$l Hamilton syringe fitted with a 0.4 mm diameter disposable needle is loaded with the bacterial suspension avoiding trapped air bubbles. Between inoculations with different bacterial strains the needle is discarded and the syringe flushed out 3 times with 100% ethanol and 3 times with sterile distilled water. 10-day old plants are inoculated by (i) abrasion of an upper leaf, applying 20 $\mu$l of suspension, and rubbing in with carborundum powder until the leaf appears wet all over, (ii) injection of 10 $\mu$l of bacterial suspension into the central part of the plant either just above the first leaf blade, or 1 cm below the first leaf blade, or at the base of the plant, in the meristematic region where adventitious roots later begin to appear. Three-day old seedlings are injected with 10 $\mu$l of bacterial suspension in different ways by (i) pushing the needle down through the apical tip of the coleoptile to the coleoptilar node, (ii) injecting 2 mm below the apical tip of the coleoptile, (iii) 2 mm above the coleoptilar node, (iv) at the coleoptilar node, (iv) 2 mm below the coleoptilar node, (v) at the scutellar node, and by pushing the needle up through the primary root to a region close to the scutellar node. Ten $\mu$l is used as a standard inoculum of bacterial suspension, but only 1–2 $\mu$l routinely remains in the inoculation site, the rest is forced out, usually coming out from the point of entry of the inoculating needle. Following inoculation seedlings are planted immediately in damp soil, incubated as before (Grimsley et al. (1987) Nature 325:177–179), and observed daily for the appearance of symptoms of viral infection, characterized by the appearance of yellow spots and/or stripes at the base of new leaves.

Histology: Plant pieces containing the site of injection are collected, fixed in Carnoy's fluid (60% ethanol, 30% chloroform, 10% glacial acetic acid) overnight, dehydrated in a series of 50%, 75% and 100% ethanol, and then prepared for the infiltration of paraffin wax in a series of 25%, 50%, 75% and 100% xylene in ethanol (at least 30 min is allowed for each of the serial steps). Finally they are embedded in paraffin at 65 ° C. and cut with a microtome into slices of 15–35 $\mu$m depending upon the size of the plant pieces. All procedures are carried out according to Sass (Sass, J. E. (1958). Botanical Microtechnique, p. 14–54. The Iowa State University Press, Ames, Iowa.).

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for targeting the insertion of a nucleotide sequence of interest to a specific chromosomal site within the genome of a plant cell, said method comprising:
    transforming said plant cell with a transfer cassette, said transfer cassette comprises said nucleotide sequence of interest and said transfer cassette is flanked by or comprises non-identical recombination sites;
    wherein said plant genome comprises a target site comprising non-identical recombination sites which correspond to the non-identical recombination sites of said transfer cassette; and,
    providing a recombinase that recognizes and implements recombination at the non-identical recombination sites;
    wherein said transfer cassette is introduced into said plant cell by a transformation method which minimizes random integration of the transfer cassette into the genome of the plant cell and results in about 5 or fewer random integration events.

2. The method of claim 1, wherein said nucleotide sequence of interest is flanked by said non-identical recombination sites.

3. The method of claim 1, wherein said transformation method is an Agrobacterium-mediated method.

4. The method of claim 3, wherein said transformation method comprises a modified Agrobacterium-mediated transformation method utilizing a modified T-DNA integration function.

5. The method of claim 4, wherein said Agrobacterium-mediated method contains a modified VirD2 gene.

6. The method of claim 5, wherein said plant cell is a dicotyledonous plant cell.

7. The method of claim 1, wherein said plant cell is a monocotyledonous cell.

8. The method of claim 7, wherein said monocotyledonous cell is a maize cell.

9. A modified plant made by the method of claim 7.

10. A modified plant made by the method of claim 8.

11. Seed of the plant of claim 10.

12. Seed of the plant of claim 9.

13. The method of claim 1, wherein said transformation method is a virus based method.

14. The method of claim 1, wherein said non-identical recombination sites are selected from the group consisting of FRT, mutant FRT, LOX, and mutant LOX sites.

15. The method of claim 1, wherein said sites are a FRT site and a mutated FRT site.

16. The method of claim 15, wherein said mutant FRT site is FRT5 (SEQ ID NO: 3), FRT 6 (SEQ ID NO: 4) or FRT 7 (SEQ ID NO: 5).

17. The method of claim 1 wherein said recombinase is provided by genetically transforming said plant with an expression cassette containing a nucleotide sequence encoding said recombinase.

18. The method of claim 17, wherein said recombinase is FLP.

19. The method of claim 18, wherein said FLP has been synthesized using maize preferred codons.

20. The method of claim 1, wherein said transformation method results in less than 3 random integration events.

21. The method of claim 1 wherein said plant cell is a dicot.

22. A method for targeting the insertion of a nucleotide sequence of interest to a specific chromosomal site within the genome of a plant cell, said method comprising:
transforming said plant cell with a transfer cassette, said transfer cassette comprises said nucleotide sequence of interest and said transfer cassette is flanked by or comprises non-identical recombination sites;
wherein said plant cell genome comprises a target site comprising non-identical recombination sites which correspond to the non-identical recombination sites of said transfer cassette; and,
contacting said non-identical sites with a recombinase that recognizes and implements recombination at the non-identical recombination sites; wherein said transfer cassette is introduced into said plant cell by a viral transformation method which minimizes random integration of the transfer cassette into the genome of the plant cell.

23. A plant having stably incorporated into its genome less than about 5 transfer cassettes, wherein said transfer cassette comprises a nucleotide sequence of interest and is flanked by or comprises non-identical FRT recombination sites.

24. The plant of claim 23, wherein said plant is a monocot.

25. The plant of claim 24, wherein said monocot is maize.

26. The plant of claim 23, wherein said plant is a dicot.

27. The transformed seed of the plant of claim 23.

28. The plant of claim 23, wherein said non-identical recombination sites are a FRT site and a mutant FRT site.

29. The plant of claim 23, wherein the genome further comprises an expression cassette containing a nucleotide sequence encoding a FLP recombinase.

30. The plant of claim 29, wherein said FLP recombinase comprises maize preferred condons.

31. A plant cell having stably incorporated into its genome less than about 5 transfer cassettes, wherein said transfer cassette comprises a nucleotide sequence of interest and is flanked by or comprises non-identical FRT recombination sites.

32. The plant cell of claim 31, wherein said plant cell is from a monocot.

33. The plant cell of claim 32, wherein said monocot is maize.

34. The plant cell of claim 33, wherein said plant cell is from a dicot.

35. The plant cell of claim 31, wherein said non-identical recombination sites are a FRT site and a mutant FRT site.

36. The plant cell of claim 31, wherein the genome further comprises an expression cassette containing a nucleotide sequence encoding a FLP recombinase.

37. The plant cell of claim 36, wherein said FLP recombinase comprises maize preferred condons.

38. A plant having stably incorporated into its genome less than about 5 transfer cassettes, wherein said transfer cassette comprises a nucleotide sequence of interest and is flanked by or comprises non-identical recombination sites, wherein said plant is a monocot.

39. The plant of claim 38, wherein said non-identical recombination sites are selected from the group consisting of a FRT site, a mutant FRT site, a LOX site, and a mutant LOX site.

40. The plant of claim 39, wherein said non-identical recombination sites are selected from the group consisting of a FRT and a mutant FRT site.

41. The plant of claim 38, wherein the genome further comprises an expression cassette containing a nucleotide sequence encoding a recombinase.

42. A plant cell having stably incorporated into its genome less than about 5 transfer cassettes, wherein said transfer cassette comprises a nucleotide sequence of interest and is flanked by or comprises non-identical recombination sites, wherein said plant is a cell is from a monocot.

43. The plant cell of claim 42, wherein said non-identical recombination sites are selected from the group consisting of a FRT site, a mutant FRT site, a LOX site, and a mutant LOX site.

44. The plant cell of claim 43, wherein said non-identical recombination sites are selected from the group consisting of a FRT and a mutant FRT site.

45. The plant cell of claim 42, wherein the genome further comprises an expression cassette containing a nucleotide sequence encoding a recombinase.

46. A modified plant made by the method of claim 15.

47. Seed of the plant of claim 46.

* * * * *

UNITED STATES PATENT AND TRADEMARK OFFICE
CERTIFICATE OF CORRECTION

PATENT NO. : 6,331,661 B1
DATED : December 18, 2001
INVENTOR(S) : Baszczynski et al.

It is certified that error appears in the above-identified patent and that said Letters Patent is hereby corrected as shown below:

Column 3,
Line 67, cancel "2".

Column 15,
Line 53, "condons" should read -- codons --.

Column 16,
Line 10, "claim 33" should read -- claim 31 --;
Line 19, "condons" should read -- codons --.

Signed and Sealed this

Twentieth Day of August, 2002

Attest:

JAMES E. ROGAN
Attesting Officer    Director of the United States Patent and Trademark Office

SEQUENCE LISTING

<160> NUMBER OF SEQ ID NOS: 5

<210> SEQ ID NO 1
<211> LENGTH: 34
<212> TYPE: DNA
<213> ORGANISM: Unknown
<220> FEATURE:
<223> OTHER INFORMATION: Description of Unknown Organism:Constructed by
      synthesizing, annealing and ligating complementary
      oligonucleotides or by creating primers for PCR amplification

<400> SEQUENCE: 1
gaagttccta ttctctagaa agtataggaa cttc                                34

<210> SEQ ID NO 2
<211> LENGTH: 69
<212> TYPE: DNA
<213> ORGANISM: Unknown
<220> FEATURE:
<223> OTHER INFORMATION: Description of Unknown Organism:Constructed by
      synthesizing, annealing and ligating complementary
      oligonucleotides or by creating primers for PCR amplification

<400> SEQUENCE: 2

-continued

```
ccatggctag cgaagttcct attccgaagt tcctattctc tagaaagtat aggaacttca      60
gatctcgag                                                              69

<210> SEQ ID NO 3
<211> LENGTH: 69
<212> TYPE: DNA
<213> ORGANISM: Unknown
<220> FEATURE:
<223> OTHER INFORMATION: Description of Unknown Organism:Constructed by
      synthesizing, annealing and ligating complementary
      oligonucleotides or by creating primers for PCR amplification

<400> SEQUENCE: 3
ccatggctag cgaagttcct attccgaagt tcctattctt caaaaggtat aggaacttca      60
gtactcgag                                                              69

<210> SEQ ID NO 4
<211> LENGTH: 72
<212> TYPE: DNA
<213> ORGANISM: Unknown
<220> FEATURE:
<223> OTHER INFORMATION: Description of Unknown Organism:Constructed by
      synthesizing, annealing and ligating complementary
      oligonucleotides or by creating primers for PCR amplification

<400> SEQUENCE: 4
ccatggctag cgaagttcct attccgaagt tcctattctt caaaaagtat aggaacttca     60
gacgtcctcg ag                                                         72

<210> SEQ ID NO 5
<211> LENGTH: 72
<212> TYPE: DNA
<213> ORGANISM: Unknown
<220> FEATURE:
<223> OTHER INFORMATION: Description of Unknown Organism:Constructed by
      synthesizing, annealing and ligating complementary
      oligonucleotides or by creating primers for PCR amplification

<400> SEQUENCE: 5
ccatggctag cgaagttcct attccgaagt tcctattctt caataagtat aggaacttca     60
ctagttctcg ag                                                         72
```